(12) United States Patent
Cheng-Shorland et al.

(10) Patent No.: US 12,423,193 B1
(45) Date of Patent: Sep. 23, 2025

(54) WEB-BASED ELECTRONIC MEDICAL RECORD DATABASE BACKUP, BUSINESS CONTINUITY AND CYBER RESILIENCE DURING EMR DOWNTIME

(71) Applicant: SHELTERZOOM CORP., New York, NY (US)

(72) Inventors: Chao Cheng-Shorland, New York, NY (US); Allen Alishahi, New York, NY (US)

(73) Assignee: SHELTERZOOM CORP., New York, NY (US)

( * ) Notice: Subject to any disclaimer, the term of this patent is extended or adjusted under 35 U.S.C. 154(b) by 0 days.

(21) Appl. No.: 18/598,820

(22) Filed: Mar. 7, 2024

(51) Int. Cl.
| | |
|---|---|
| *G06F 17/00* | (2019.01) |
| *G06F 11/14* | (2006.01) |
| *G16H 10/60* | (2018.01) |

(52) U.S. Cl.
CPC ......... *G06F 11/1464* (2013.01); *G16H 10/60* (2018.01); *G06F 2201/80* (2013.01)

(58) Field of Classification Search
CPC .. G06F 11/1464; G06F 2201/80; G16H 10/60
See application file for complete search history.

(56) References Cited

U.S. PATENT DOCUMENTS

| | | | | |
|---|---|---|---|---|
| 10,216,363 | B2 * | 2/2019 | Gronow | G06F 3/0482 |
| 11,334,570 | B2 * | 5/2022 | Nguyen | G16H 10/60 |
| 12,135,808 | B2 * | 11/2024 | Cheng-Shorland | G06F 21/64 |
| 2001/0049610 | A1 * | 12/2001 | Hazumi | G16H 40/67 |
| | | | | 705/3 |

(Continued)

OTHER PUBLICATIONS

Meiquan Wang et al., Blockchain-based Secure Medical Data Management and Disease Prediction. In Proceedings of the Fourth ACM International Symposium on Blockchain and Secure Critical Infrastructure. Association for Computing Machinery, 71-82, <https://doi.org/10.1145/3494106.3528678>, May 2022.*

(Continued)

*Primary Examiner* — Greta L Robinson
(74) *Attorney, Agent, or Firm* — Sterne, Kessler, Goldstein & Fox, P.L.L.C.

(57) ABSTRACT

The web-based EMR backup system empowers Healthcare facility administrators by building cyber resilience to ransomware threats, data breaches, power outages, or planned downtimes. A web-based EMR backup process is provided in embodiments of the invention, enabling administrators to activate a web-based EMR system in the event of a debilitating cyber-attack, power outage, or planned downtime, that allows healthcare professionals to maintain their daily workflow using the web-based EMR backup system in order to maintain business continuity and clinical resiliency. The web-based EMR system minimizes the risks that would arise due to errors generated because of traditional record keeping methods, such as manual record keeping, while also maintaining the workflow efficiencies modern EMR systems provide. The web-based EMR backup system synchronizes any changes made during the cyber-threat, power outage, or planned downtime once the main EMR is restored to ensure data consistency and provide significant financial savings by preventing the need to reconcile the two databases by hand.

24 Claims, 13 Drawing Sheets

(56) References Cited

U.S. PATENT DOCUMENTS

| | | | |
|---|---|---|---|
| 2006/0004605 A1 | 1/2006 | Donoghue et al. | |
| 2016/0171231 A1* | 6/2016 | Evans | G08B 25/14 726/17 |
| 2018/0374564 A1 | 12/2018 | Kusuma et al. | |
| 2020/0168307 A1* | 5/2020 | Chen | G06F 16/22 |
| 2021/0110919 A1 | 4/2021 | Garner et al. | |
| 2021/0335461 A1* | 10/2021 | Koutsoudis | G06F 21/32 |
| 2024/0070627 A1 | 2/2024 | Galterio | |

OTHER PUBLICATIONS

Hongjiao Wu, Ashutosh Dhar Dwivedi, and Gautam Srivastava. 2021. Security and Privacy of Patient Information in Medical Systems Based on Blockchain Technology. ACM Trans. Multimedia Comput. Commun. Appl. 17, 2s, Article 60 (Jun. 2021), 17 pages. <https://doi.org/10.1145/3408321>, Jun. 2021.*

Zhiyong Li et al., An EMR Sharing and Privacy Protection Mechanism Based on Medical Consortium Blockchain. In Proceedings of the 2020 6th International Conference on Computer and Technology Applications. Association for Computing Machinery, 160-164. <https://doi.org/10.1145/3397125.3397153>, Apr. 2020.*

International Search Report and Written Opinion for International Application No. PCT/US2025/018259, mailed May 12, 2025, 12 pages.

* cited by examiner

Organization Name — 200

- User Management
- Group Management
- Enterprise Administrators
- Account Settings
- Log Extract

[ Spare Tire ]

---

Spare Tire

| Overview | Re-Sync |

⚠ Alert! Main EMR Outage Detected

Spare Tire

Status ● Active ← 212

Last Activity As of May 2, 2023, 11 AM EST

┌─────────────────────┐
│ April 25, 2023      │
│ 09:01:01: EST       │
│ Spare Tire          │
│ Last Activated      │
└─────────────────────┘

┌──────────────────┐
│ 6                │
│ System Outages   │
│ Last Month       │
│ 33% ↑            │
└──────────────────┘

┌──────────────────┐
│ 60               │
│ System Outages   │
│ Last 12 Months   │
│ 20% ↑            │
└──────────────────┘

Source Database Type: Epic EMR

Source Database Name: EPIC/MAIN/DB1

PORTAL URRLs: www.abchospital/dashboard  ⊕ ADD URL

1006 Patient Name
Age: 23  Sex: Male  MRN: 123456789
DOB:01/05/2000

1002 [Search 🔍]

[Call]  [Email]  [+ Add Clinical Notes]

1008 Snapshot  Intake  Chart Review  Results Review  Allergies  Problem List  Medications  Immunizations  Demographics  Wrap Up 1010A
Letters
Templates
+ Md To Recipient List, W/Prog Note
+ Md To Recipient List, Custom Text
+ Md To Referring Md/Prog Note

1012

1010B
Billing Code
ADD A CODE  +
36415 – Collection of venous blood by venipuncture 1010C
Patient Instructions
1. ...
2. ...
3. ...

Home Page
Patients
Help & Support

WEB-BASED ELECTRONIC MEDICAL RECORD DATABASE BACKUP, BUSINESS CONTINUITY AND CYBER RESILIENCE DURING EMR DOWNTIME

BACKGROUND

Field

The present invention is in the technology of Electronic Medical Record keeping systems, and pertains more particularly to a system for integrating existing Electronic Medical Record systems with a secure web-based backup system.

Related Art

There have been significant advances within the medical industry over the last decade. One of those advances is the development and implementation of Electronic Medical Record ("EMR") keeping systems. Traditionally record keeping within a healthcare facility was done using pen and paper. A method that introduced significant medical errors within healthcare facilities and increased the time needed to process medical events.

A Modern EMR systems has many benefits over the traditional record keeping methods. EMR systems provide patients with better care than traditional record keeping by alerting medical staff of issues related to drug-to-drug/drug-to-allergy interactions, improper dosing, duplicative therapies, and the patient's status. EMR systems also provide increased accuracy. Traditional record keeping methods led to problems associated with paper-based prescribing, such as illegible handwriting, misread abbreviations and misread dosages.

Modern EMR systems enhance workflow efficiency by streamlining treatment into a single workflow that assigns specific tasks to each medical staff member. EMR systems minimize fraud and drug diversion by securely transmitting prescription from the provider to the pharmacy. EMR systems also prevent drug abuse and misuse by enabling physicians to examine a patients' medical history to determine if a patient is "doctor shopping" or has drug-abusing behaviors.

Modern research suggests that the implementation of EMR systems has led to a drastic decrease in the amount of medical errors within a healthcare facility while increasing workflow efficiency. With some healthcare facilities, experiencing less than ⅓ of the medical errors while using an EMR system as compared to traditional record keeping. These benefits have also led to an increase in revenue due to increased workflow efficiency leading to an increase in the amount of patients treated and a reduction in operating expenses by reducing legal and administrative fees.

As demonstrated above, the antiquated system of preparing, reading, signing and filing hard-copy paper records is time-consuming, wasteful, and a risk to human life. It is, therefore, extremely important for healthcare facilities to maintain access to their EMR system at all times to prevent the issues stated above.

In the event of network outages, however, most healthcare facilities revert back to traditional pen and paper record keeping methods. Today, many healthcare facilities are targets of cyber-attacks that cause network outages. The most common and lucrative form of cybersecurity attack within the healthcare industry is called a ransomware attack. A ransomware attack is a type of cybersecurity attack that is caused by a type of malware that encrypts, or renders inaccessible, the infected data until a ransom is paid to the malicious actor. During a ransomware attack, companies can be forced to pay ransoms ranging from tens of millions to hundreds of millions of dollars. Ransomware attacks typically aim to take control of important files in a computing system by cryptographic encryption, with such files including user files in home folders and system files in system folders. In 2022 alone, there were around 500 million ransomware attempts. A ransomware attack within healthcare industry can result in significant disruptions to efficiency while also leading to potentially life-threatening events related to a lack of access to medical records. Both of which will lead to a significant increase in operating costs.

Additionally, there is no guarantee that paying the malicious actor of the ransomware attack will result in the return of stolen or uncorrupted files. For these reasons, preventing ransomware attacks is increasingly important for the healthcare industry.

The most common method of minimizing ransomware attacks employs the concept of data replication, which periodically creates backup images of the entire network and stores them in either locally or in a remote network. This strategy, however, is still prone to failure. During a ransomware attack, the malware is stored within the network. If a backup image is created while the malware is present, that backup image will be contaminated. To address this, most systems store multiple backup images in the hope that one of them will not contain the malicious code. Thus, in order to increase the likelihood that there is a clean backup image, one need to drastically increase the number and frequency of backup images created. This leads to a drastic increase in the amount of storage capacity and processing power needed to effectively operate these systems. Which also leads to higher deployment and operating costs.

What is clearly needed is a web-based EMR backup system that operates outside of the main healthcare facilities' network that can be activated during an outage in order to maintain operational status and provide a web-based EMR interface to healthcare employees until the outage is resolved.

BRIEF SUMMARY

In an embodiment of the invention a computer implemented method is provided, comprising receiving by one or more of a plurality of internet-connected servers and an EMR backup server EMR data, storing by one or more of a plurality of internet-connected servers and the EMR backup server the EMR data, providing by the EMR backup server a web portal, connecting a user device to the EMR backup server, receiving via the user device an admin user selection of an activation button, in response to receiving the admin user selection of the activation button transmitting from the EMR backup server a location identifier corresponding to the web portal to the user device, displaying by the EMR backup server the web portal wherein the web portal includes a dashboard wherein the dashboard is generated by the EMR data and includes one or more input fields for a user to submit additional EMR data, generating by the EMR backup server a hash of the EMR data, storing by the EMR backup server the hash on a blockchain.

In one embodiment of the method, the computer implemented method comprises receiving via the user device additional EMR data wherein the additional EMR data is provided by a user input in the one or more input fields, generating by the EMR backup server a reintegration flag, updating by the EMR backup server the EMR data based on the additional EMR data, generating by the EMR backup server a hash of the updated EMR data, storing by the EMR backup server the hash of the updated EMR data on a blockchain.

In one embodiment of the method, the reintegration flag is a hash reference to an EMR transaction that validates the EMR transaction on a blockchain. The reintegration flag is used to determine if the EMR data, additional EMR data, or updated EMR data is valid and reconcile EMR data within the database.

In one embodiment of the method, the computer implemented method comprises receiving via the user device an admin user selection of a deactivation button, in response to receiving the admin user selection of the deactivation button transmitting from the EMR backup server to the one or more of a plurality of internet-connected servers a request to reintegrate the EMR data stored on the EMR backup server with the EMR data stored on the one or more of a plurality of internet-connected servers.

In one embodiment of the method, the computer implemented method comprises receiving by the one or more of a plurality of internet-connected servers a request to reintegrate the EMR data, in response to receiving the request to reintegrate the EMR data requesting from the EMR backup server the reintegration flag wherein the reintegration flag identifies EMR data that has been added or updated during a network outage, generating by the one or more of a plurality of internet-connected servers an updated EMR database based on the reintegration flag, storing by the one or more of a plurality of internet-connected servers the updated EMR database.

In one embodiment of the method, the dashboard includes a clinical notes data field that is electronically signed using a hash of a user's profile and the EMR data.

In one embodiment of the method, the dashboard includes one or more electronic forms.

In one embodiment of the method, the electronic forms includes templates for patient letters and instructions that are automatically generated using the EMR data.

In another aspect of the invention a web-based EMR backup system is provided, comprising an EMR backup server registering one or more of a plurality of Internet-connected servers, the one or more of the plurality of Internet-connected servers hosting respective websites, the EMR backup server providing configurable coded instructions to the one or more of the plurality of Internet-connected servers for displaying an activation button on the respective websites, a user device connected to the one or more of the plurality of Internet-connected servers, wherein each of the one or more of the plurality of Internet-connected servers are configured to display the activation button on the Internet-connected server's respective website using the configurable coded instructions received from the EMR backup server, receive via the user device a user selection of the activation button via the Internet-connected server's respective website, in response to receiving the admin user selection of the activation button transmit a web portal to the user device wherein the web portal includes a dashboard that is generated by EMR data and includes one or more input fields for a user to submit additional EMR data, generate a hash of the EMR data, store the hash on a blockchain.

In one embodiment of the system, the web-based EMR backup system comprises receiving via the user device additional EMR data wherein the additional EMR data is provided by a user input in the one or more input fields, generating by the EMR backup server a reintegration flag, updating by the EMR backup server the EMR data based on the additional EMR data, generating by the EMR backup server a hash of the updated EMR data, storing by the EMR backup server the hash of the updated EMR data on a blockchain.

In one embodiment of the system, the web-based EMR backup system comprises receiving via the user device an admin user selection of an deactivation button, in response to receiving the admin user selection of the deactivation button transmitting from the EMR backup server to the one or more of a plurality of internet-connected servers a request to reintegrate the EMR data stored on the EMR backup server with the EMR data stored on the one or more of a plurality of internet-connected servers.

In one embodiment of the system, the web-based EMR backup system comprises In one embodiment of the method, the computer implemented method comprises receiving by the one or more of a plurality of internet-connected servers a request to reintegrate the EMR data, in response to receiving the request to reintegrate the EMR data requesting from the EMR backup server the reintegration flag wherein the reintegration flag identifies EMR data that has been added or updated during a network outage, generating by the one or more of a plurality of internet-connected servers an updated EMR database based on the reintegration flag, storing by the one or more of a plurality of internet-connected servers the updated EMR database.

In one embodiment of the system, the dashboard includes a clinical notes data field that is electronically signed using a hash of a user's profile and the EMR data.

In one embodiment of the system, the dashboard includes one or more electronic forms.

In one embodiment of the system, the electronic forms includes templates for patient letters and instructions that are automatically generated using the EMR data.

In another aspect of the invention a non-transitory computer-readable device having instructions stored thereon that, when executed by at least one computing device, cause the at least one computing device to perform operations is provided comprising receiving by one or more of a plurality of internet-connected servers and an EMR backup server EMR data, storing by one or more of a plurality of internet-connected servers and the EMR backup server the EMR data, providing, by the EMR backup server a web portal, connecting a user device to the EMR backup server, receiving via the user device an admin user selection of an activation button, in response to receiving the admin user selection of the activation button transmitting from the EMR backup server a location identifier corresponding to the web portal to the user device, displaying, by the EMR backup server the web portal wherein the web portal includes a dashboard wherein the dashboard is generated by the EMR data and includes one or more input fields for a user to submit additional EMR data, generating by the EMR backup server a hash of the EMR data, storing by the EMR backup server the hash on a blockchain.

In one embodiment of the system, the web-based EMR backup system comprises receiving via the user device additional EMR data wherein the additional EMR data is provided by a user input in the one or more input fields, generating by the EMR backup server a reintegration flag, updating by the EMR backup server the EMR data based on the additional EMR data, generating by the EMR backup server a hash of the updated EMR data, storing by the EMR backup server the hash of the updated EMR data on a blockchain.

In one embodiment of the system, the web-based EMR backup system comprises receiving via the user device an admin user selection of a deactivation button, in response to receiving the admin user selection of the deactivation button transmitting from the EMR backup server to the one or more of a plurality of internet-connected servers a request to reintegrate the EMR data stored on the EMR backup server with the EMR data stored on the one or more of a plurality of internet-connected servers.

In one embodiment of the system, the web-based EMR backup system comprises In one embodiment of the method, the computer implemented method comprises receiving by the one or more of a plurality of internet-connected servers a request to reintegrate the EMR data, in response to receiving the request to reintegrate the EMR data requesting from the EMR backup server the reintegration flag wherein the reintegration flag identifies EMR data that has been added or updated during a network outage, generating by the one or more of a plurality of internet-connected servers an updated EMR database based on the reintegration flag, storing by the one or more of a plurality of internet-connected servers the updated EMR database.

In one embodiment of the system, the dashboard includes a clinical notes data field that is electronically signed using a hash of a user's profile and the EMR data.

In one embodiment of the system, the dashboard includes one or more electronic forms.

In one embodiment of the system, the electronic forms includes templates for patient letters and instructions that are automatically generated using the EMR data.

BRIEF DESCRIPTION OF THE DRAWINGS

FIG. 3 illustrates a display of an active selection of a web-based EMR backup system in an embodiment of the invention.

Figure 5:
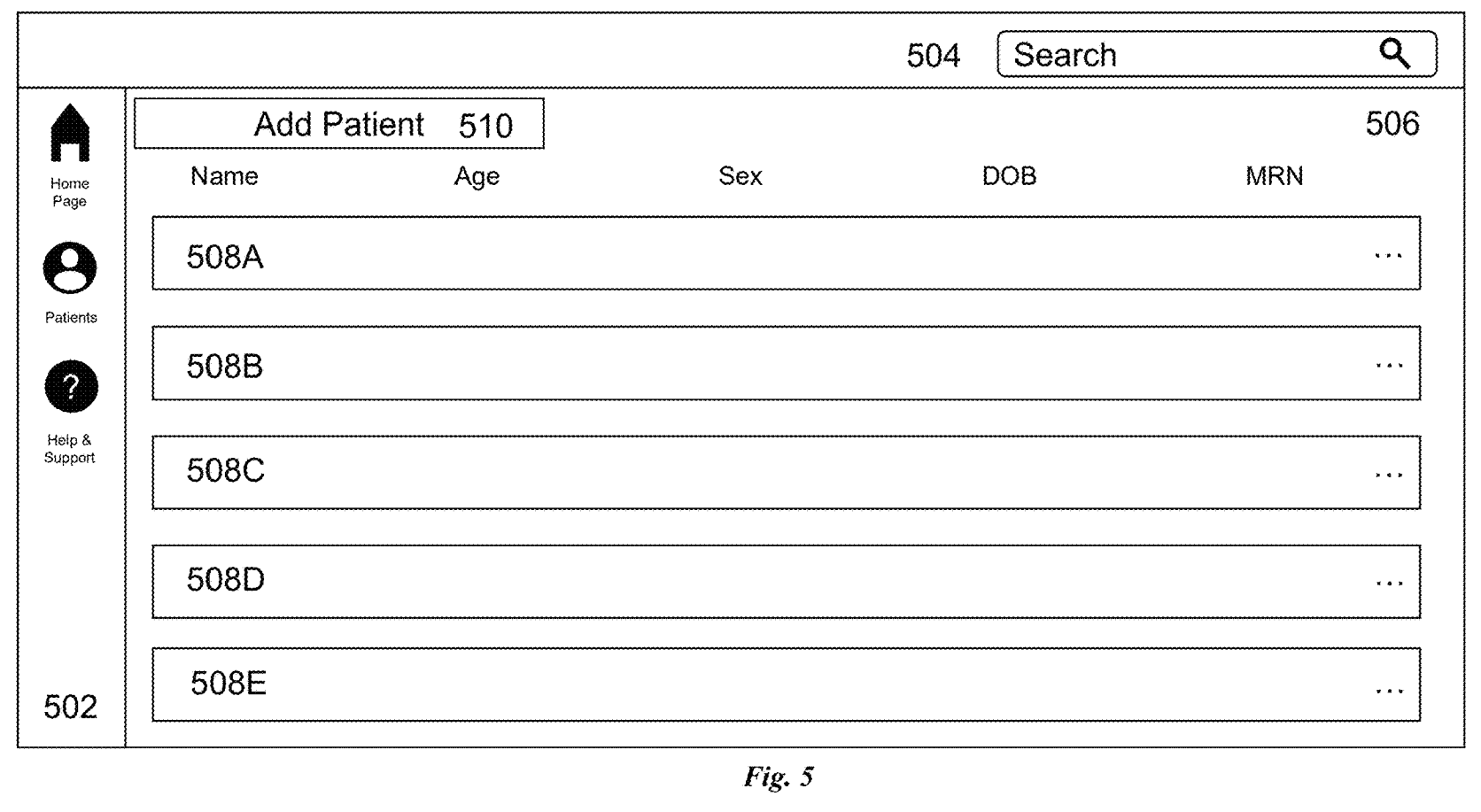

FIG. 5 illustrates a display of a patient portal in an embodiment of the invention.

FIG. 6 illustrates a display of an editable electronic form for adding patients in an embodiment of the invention.

FIG. 7 illustrates a display of a snapshot of a patient profile in an embodiment of the invention.

FIG. 8 illustrates a display of a patient intake landing page in an embodiment of the invention.

FIG. 9 illustrates a display of an electronic patient chart in an embodiment of the invention.

FIG. 10 illustrates a display of a patient discharge portal in an embodiment of the invention.

FIG. 11 illustrates a display of an electronic template in an embodiment of the invention.

DETAILED DESCRIPTION

Figure 1:
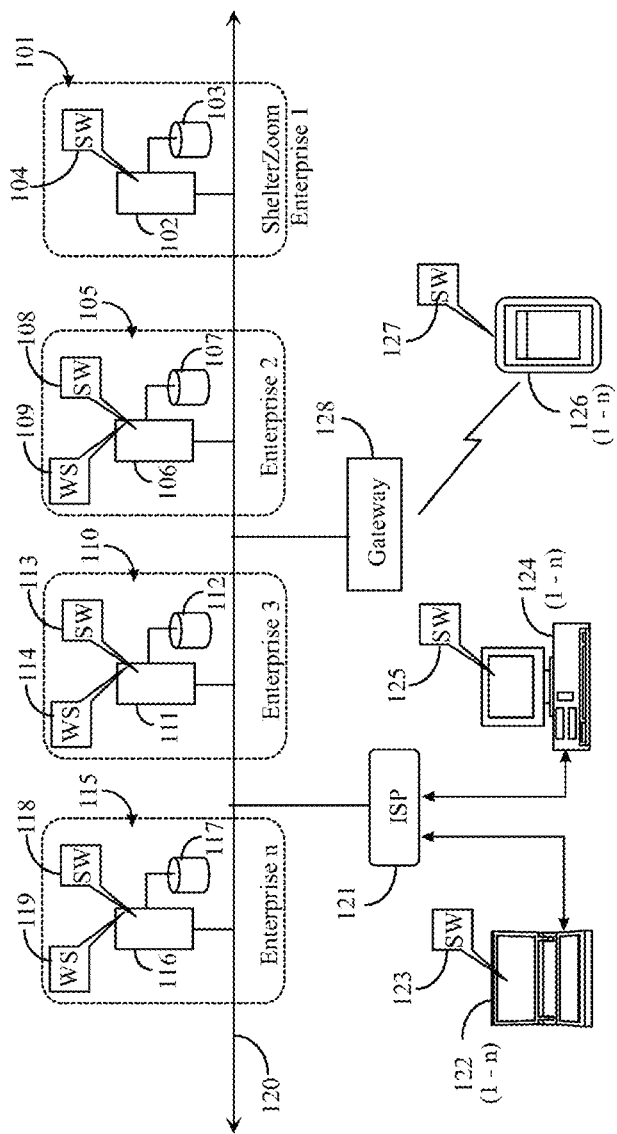
FIG. 1 is an architectural diagram of a system in one embodiment of the present invention.

The inventors in the present application offer a comprehensive system providing a web-based Electronic Medical Record ("EMR"), or sometimes referred to as a Electronic Health Record ("EHR"), backup system that is secure and remote from a healthcare facilities' main EMR system.

The invention in various embodiments and aspects provides an unprecedented speedy, simple and effective EMR backup system. The web-based EMR backup system in embodiments of the invention empowers Healthcare facility administrators to ensure continued operation of a modern EMR system in the event of a debilitating cyber-attack, power outage, or planned downtime. A web-based EMR backup process is provided in embodiments of the invention as well, enabling administrators to activate a web-based EMR system in the event of a debilitating cyber-attack, that allows healthcare professionals to maintain their daily workflow using the web-based EMR backup system. The web-based EMR system minimizes the risks that would arise due to errors generated because of traditional record keeping methods, while also maintaining the workflow efficiencies modern EMR systems provide.

The benefits of a web-based EMR system, disclosed throughout, when compared to traditional EMR backup systems are outlined below:

|  | Web-Based EMR | Traditional EMR Backup Solutions |
|---|---|---|
| Operational Continuity | Yes, almost instantaneous | No, 24 to a few weeks' until traditional EMR backups are evaluated and back online |
| Data Contamination | Upholds the integrity of data through the use of secure networks | Traditional backup data stores may be contaminated. Leading increased downtime and cost evaluating data stores. |
| Patient Lives | Maintain high levels of patient care due to near instantaneous operational continuity. Leading to less deaths as a result of operational resources being down. | Likely to lead to patient deaths due to a lack of operational continuity and loss of operational resources. |
| Efficiency and Time Saving | Clinical notes and patient charts are maintained online and sync'd back to the main EMR system. Allowing a faster and cheaper reintegration process | Manual charting leads to increased costs and time during the reintegration of EMR data. Manual charting also leads to an increase in the amount of manual errors existing in a system. |
| Change Management | Minimum change management with user experience similar to that of main EMR system | Manual Process |

-continued

| | Web-Based EMR | Traditional EMR Backup Solutions |
|---|---|---|
| Cost | Save millions of dollars per attack by decreasing operational downtime and preventing the need to pay a ransom. | High cost during the downtime due to the need to evaluated contaminated data stores, identify the point of the breach, etc. Also will likely need to pay a ransom to end the quicker and restore operational efficiency sooner. |
| Revenue Cycle Continuity | Allows for revenue recovery due to invoice and bill operational continuity. Thus, allowing the hospital to maintain financial solvency. | Lacks a way to administer invoices or bills. Lease to inefficiencies, delays, and inaccuracies that impact financial continuity. |

In different aspects of the invention healthcare facility readiness and resilience to various types of cyber-attacks are improved by incorporating a web-based EMR backup system.

FIG. 1 is an architectural diagram of a system in one embodiment of the present invention. In FIG. 1 a plurality of enterprises or servers hosting digitized platforms that are interconnected in a wide area network represented by backbone 120. The network in many embodiments of the invention is the well-known Internet network, and backbone 120 may be considered the Internet backbone, representing all of the interconnected networks and subnetworks that make up the Internet. An enterprise 101, labeled ShelterZoom Enterprise is shown connected to the network, with a server 102 executing software (SW) 104 coupled to a data repository 103. ShelterZoom is a name adopted by the inventors to represent the controlling enterprise in many embodiments of the present invention.

A first enterprise labeled Enterprise 1 is shown, having a server 106 connected to the Internet and coupled to a data repository 107. Server 106 executes SW 108, and also presents on the network a web site (WS) 109. A second enterprise labeled Enterprise 2 is shown, having a server 111 connected to the Internet and coupled to a data repository 112. Server 111 executes SW 113, and also presents on the network a web site (WS) 114. A third enterprise labeled Enterprise n is shown, having a server 111 connected to the Internet and coupled to a data repository 117. Server 116 executes SW 118, and also presents on the network a web site (WS) 119.

The ShelterZoom enterprise is a singular platform providing data integration, digital tools and controls in many embodiments of the invention. Enterprises 2 through n represent any number of enterprises that may be interacting with ShelterZoom and other enterprises in various aspects and circumstances in embodiments of the invention. In some specific cases these enterprises may be different systems or entities within the interconnected healthcare industry, such as electronic medical record managers, cloud service providers, physicians' or specialists' offices, health insurance payers, billing services, care providers, pharmacies, clinical researchers, connected medical devices and wearable devices, healthcare corporations, and government and regulatory agencies in the healthcare industry.

In other embodiments of the invention individual ones of enterprises 2 through n may be enterprises providing EMR database services to healthcare facilities. For case of explanation, the web-based EMR backup system 101 will be described with reference to enterprise 2, a healthcare facility main EMR system 105. All disclosure relating to the main EMR system 105 is not limited solely to the interactions between enterprise 2 and the web-based EMR backup system 101 and should be extended to enterprises 2-n.

In FIG. 1 a laptop computer 122 (1-n) executing SW 123 is shown connected to the Internet network through an Internet Service Provider (ISP) 121. Similarly, a desktop computer 124 (1-n) is shown also connected to the Internet through ISP 121. These computer platforms represent many such platforms that may be utilized by individuals, such as medical administrators or staff, to access enterprises 2-n to perform their daily tasks (e.g., billing, patient intake, recording patient vitals, reviewing medical charts, reviewing doctor's orders, updating a patient's medical history, monitor the status of the EMR system, etc.). A smartphone 126 (1-n) is also shown in FIG. 1 connecting to the internet through a gateway 128, representing any number of smartphones that may be used by individuals to interact with individual ones of enterprises 2-n.

System-Level

In the architecture of FIG. 1 at least one of the enterprises 2-n, represents a either a public or private enterprise Blockchain provider, such as for example, Ethereum, a public network, or Hyperledger Fabric, a private enterprise network, which may provide services in document/data creation, storage, and security.

In embodiments of the invention Enterprise 1 is a central hub of all services and interactions in the system. Also, in embodiments, Enterprise 1, through SW 104, provides a web site with a location identifier, Domain name and a URL, through which a medical professional, that is, essentially any authorized person seeking to access a healthcare facilities EMR data, may connect via a web browser, using a browser-enhanced platform such as shown in FIG. 1 as elements 122, 124 and 126.

In embodiments of the invention, the web-based EMR backup system 101 is continuously monitoring and replicating the EMR data in the main EMR database 105. The web-based EMR backup system 101 is also continuously monitoring and replicating the EMR data contained within the databases of enterprises 3-n. This allows the web-based EMR backup system 101 to build an accurate and up-to-date backup EMR database 103. Once an outage in the main EMR system 105 is detected, and the web-based EMR backup system 101 is activated, the web-based EMR backup system 101 operates in the place of the main EMR system 105. That is, it allows medical professionals and staff to update and add EMR data using the web-based portal illustrated in FIGS. 2-11 as a part of their normal workflow. During their normal workflow, medical professionals and staff are required to update and add new EMR data pertaining to hospital administrative tasks, medical treatments, patient intake, patient charting, etc. This new EMR data is captured by the web-based portal illustrated in FIGS. 2-11 and processed by server 102 and stored in database 103. Once the main EMR system 105 is restored, the new EMR data that was created or updated during the outage needs to be reintegrated into the main EMR systems 105's databases 107. Reintegration is performed using the Re-Sync process of web-based EMR backup system 101. Once activated, the Re-Sync process queries the main EMR system 105 to reintegrate all of the new and updated EMR data. There are many ways to reintegrate data between two databases, one example is using API calls to the main EMR system 105, a person skilled in the art would understand that the invention is not limited to only using API calls to query the main EMR system 105. Unique to the invention is its ability to synchronize changes with the main EMR system once it's restored, ensuring data consistency and tremendous time saving.

A hash reference, reintegration flag, for each EMR API transaction allows for validation for the various EMR transactions on a blockchain using the Re-Sync process.

In embodiments of the invention, EMR data duplication is performed on data images that are stored within the main EMR system 105's database 107 using one or more API calls. The web-based EMR backup system 101 may include a remote database 103, wherein the database 103 is "air-gapped" from the main EMR system 105's database 107. This aids to prevent the web-based EMR backup system 101 from replicating the malicious code that caused the main EMR system 105 to experience an outage. Similarly, the remote database 103 may include or correspond to a cloud data service provider that is isolated from the main EMR system 105 and its network. API calls are used to store the backup EMR data images such as patient records, patient charts, clinical notes, admission and discharge records, order transmittals, ambulatory workflows, patient transfer orders, bed status/sensors, and patient transfer records at the remote database 103. The API calls may be one or more industry standard or otherwise "open" (e.g., non-proprietary and available) API calls, such as for one or more APIs configured to process and communicate electronic health record (EHR) data and/or electronic medical record (EMR) data. Once the EMR data is retrieved using API calls, the web-based EMR backup system 101 may further secure the EMR data using encryption and a private or public blockchain.

In embodiments of the invention, the web-based EMR backup system 101 monitors and validates the API calls that are used to store or retrieve data during planned downtime or a cyber/ransomware attack, the web-based EMR backup system 101 does not allow access to the main EMR system 105 to prevent possible contamination. The web-based EMR backup system 101 may generate logs of the API calls and system events for future analysis. For example. an industry standard format that includes API resources, such as InterSystems FHIR Server, may be used to implement the Fast Healthcare Interoperability Resource (FHIR) format created by the Health Level Seven (HL7) International standards organization may be used.

In embodiments of the invention, the web-based EMR backup system 101 may experience a network outage cause by internet service provider issues, cyber attacks, planned downtime, or power outages. In these events, the web-based EMR backup system 101 may require the most recent EMR data image from the main EMR system 105 to restore the EMR data that was being processed prior to the outage.

Web-based EMR backup system 101 may provide a front-end user interface to allow users to create, manage, edit, and/or modify EMR data. The user interface may be a graphical user interface (GUI) that may be accessed and/or displayed on a user device 122, 124, and 126. Upon selecting the plugin, link, or widget, user device 122, 124, and 126 may use an application programming interface (API) to communicate with Web-based EMR backup system 101.

As will be further explained below, Web-based EMR backup system 101 may provide a front-end GUI including GUI elements allowing a user to modify EMR data, create documents, modify documents, manage document permissions, generate links and/or messages corresponding to documents, manage document modifications from other parties, manage a digital wallet, manage user account information and/or account roles, and/or other document interactions.

Upon receiving EMR data, web-based EMR backup system 101 may generate a link and/or token corresponding to the received EMR data. As will be further explained below, web-based EMR backup system 101 may store an encrypted version of the EMR data and/or create a link to the encrypted version of the EMR data. Web-based EMR backup system 101 may also generate a cryptographic hash of the EMR data. Using this information along with other information such as an owner identification and/or other metadata, web-based EMR backup system 101 may create an EMR data token corresponding to the EMR data. The EMR data token may represent ownership of the EMR data and/or may be transmitted to a digital wallet corresponding to the EMR data owner. Web-based EMR backup system 101 may use the EMR data token in future operations to determine access and/or modification permissions.

After generating the EMR data token, web-based EMR backup system 101 may provide the EMR data token as link. In some embodiments, web-based EMR backup system 101 may generate a link without using a EMR data token. The link may be to an address of the database 103 storing the EMR data. The link generated by web-based EMR backup system 101 may be embedded into a message being drafted by a user device 122, 124, and 126. A user device 122, 124, and 126 may indicate to web-based EMR backup system 101 to transmit the message including the EMR data link to an intended recipient. For example, this may be a user corresponding to another user device 122, 124, and 126 or another enterprise 2-n. In some embodiments, user device 122, 124, and 126 may designate the recipient using an email address, and/or other electronic identification of the intended user. web-based EMR backup system 101 may then deliver the message.

Upon receiving the message with the EMR data link, user device 122, 124, and 126 may access the EMR data link. For example, web-based EMR backup system 101 may generate an Internet browser or application view allowing the user of user device 122, 124, and 126 to select the EMR data link. After selecting this link, user device 122, 124, and 126 may connect to web-based EMR backup system 101 to access the corresponding EMR data. User device 122, 124, and 126 may interact with the EMR data based on the permissions set by an administrator or user device 122, 124, and 126. These permissions may be associated with the EMR data link. For example, the permissions may include viewing the EMR data, acknowledging receipt of the EMR data, signing the EMR data, downloading the EMR data as a file, sharing the EMR data, and/or modifying the EMR data. User device 122, 124, and 126 may interact with the EMR data according to this permission.

In some embodiments, to access the EMR data, user device 122, 124, and 126 may supply user credentials to web-based EMR backup system 101. For example, if user device 122, 124, and 126 has an account corresponding to web-based EMR backup system 101, user device 122, 124, and 126 may supply these credentials. In some embodiments, web-based EMR backup system 101 may supply the credentials on behalf of user device 122, 124, and 126. In this manner, web-based EMR backup system 101 may receive credentials corresponding to user device 122, 124, and 126 attempting to access the EMR data. As will be further explained below, this may also occur if another user device 122, 124, and 126 also attempts to access the EMR data link.

In some embodiments, web-based EMR backup system 101 may record and/or log the access of the EMR data link. Web-based EMR backup system 101 may log this access in a EMR data flow data structure. The EMR data flow data structure may be stored in memory of web-based EMR backup system 101. The EMR data flow data structure may reflect a timeline of interactions with the EMR data. The EMR data flow data structure may track user credentials corresponding to an interaction, a timestamp, and/or a type of interaction. For example, if the user is asked to acknowledge or sign the EMR data, the EMR data flow data structure may track the user credentials and/or time that the EMR data has been acknowledged and/or signed. As will be further described below, the EMR data owner may manage the EMR data flow data structure to track and/or manage access to the EMR data as the EMR data link is disseminated to additional user device 122, 124, and 126.

For example, the EMR data owner may track and/or manage permissions if user device 122, 124, and 126 forwards the EMR data link to another user device 122, 124, and 126. Web-based EMR backup system 101 may track and/or log the access in a similar manner. The EMR data owner may user device 122, 124, and 126 to view the EMR dat flow data structure and view the access and/or modification performed by another user device 122, 124, and 126. The EMR data owner may further manage permissions specific to other user devices 122, 124, and 126. In some embodiments, even though a first user device 122, 124, and 126 has not directly transmitted the EMR data link to another user device 122, 124, and 126, the first user device 122, 124, and 126 may still view a record of the access and/or modification.

Based on this configuration, web-based EMR backup system 101 may provide a decentralized manner for disseminating EMR data while retaining control and/or permissions related to downstream users. Web-based EMR backup system 101 may provide a decentralized EMR database for users of web-based EMR backup system 101. User devices 122, 124, and 126 may access web-based EMR backup system 101 to disseminate EMR data via messages. Web-based EMR backup system 101 may securely manage the EMR data and provide control over downstream access and/or modification of the EMR data.

In some embodiments, web-based EMR backup system 101 may include object storage, a web service interface, storage for Internet applications, and/or cloud computing and/or storage. In some embodiments, web-based EMR backup system 101 may use a peer-to-peer network and/or protocol for storing and/or sharing data in a distributed file system. For example, web-based EMR backup system 101 may use content-addressing to uniquely identify files in a global namespace to network user device 122, 124, and 126. In some embodiments, web-based EMR backup system 101 may use the InterPlanetary File System (IPFS) protocol and/or servers such as Amazon S3®.

Web-based EMR backup system 101 may include an interface with database 103. Database 103 may be a private or public blockchain. As will be further described below, web-based EMR backup system 101 may interface with database 103 to store data representing EMR data and/or modifications to the EMR data. This EMR data may include a cryptographic hash of EMR data and/or a link to a human-readable representation of the EMR data. The EMR data changes may be trackable and irreversible.

In some embodiments, web-based EMR backup system 101 may also manage processing tokens used to interact with database 103 and/or a blockchain. For example, web-based EMR backup system 101 may manage digital wallet information. As will be further explained below, web-based EMR backup system 101 may also manage EMR data tokens which may represent ownership and/or permissions for EMR data and/or EMR data modifications. Web-based EMR backup system 101 may facilitate the publishing of EMR data to the blockchain and/or may remove processing tokens from an account corresponding to a digital wallet to perform the publishing.

To manage EMR data, web-based EMR backup system 101 may publish the cryptographic hash of the EMR data and/or the link to the encrypted version of the EMR data. The EMR data may be encrypted using a key corresponding to the EMR data owner. Publishing the EMR data onto the blockchain may preserve the trustworthiness of the EMR data and the legitimacy of the EMR data's content. For example, the immutable nature of a blockchain may protect against unauthorized EMR data modifications or tampering. Further, the cryptographic hash may preserve privacy and may prevent other users of the blockchain from viewing confidential information.

In some embodiments, the EMR data token may indicate that a recipient should acknowledge or sign an EMR data modification. EMR data modification can be any modification to EMR data illustrated within FIGS. 2-11 and discussed throughout, such as, after creating clinical notes, submitting new patient orders, administering medication, charting new patient vitals, etc. After accessing the link, web-based EMR backup system 101 may identify an encrypted version of the EMR data. The web-based EMR backup system 101 may then decrypt the encrypted EMR data using a digital signature key corresponding to the recipient. The recipient may provide a digital signature to confirm the acceptance. This digital signature may also be keyed to the recipient to provide verification and additional trustworthiness that the signature is legitimate and protected against interference or tampering. In some embodiments, the digital signature may also be reflected in the human-readable portion of the EMR data.

In some embodiments, the digital signature may be a modification to the EMR data. Web-based EMR backup system 101 may manage this modification in a manner similar to generating EMR data so that the modified EMR data may be preserved using database 103. For example, the signed EMR data may be encrypted and stored as a modified version of the EMR data. Web-based EMR backup system 101 may generate a corresponding link to this encrypted version of the signed EMR data and/or generate a cryptographic hash of the signed EMR data. Web-based EMR backup system 101 may create a EMR data token corresponding to the signed EMR data. Web-based EMR backup system 101 may publish the hash and/or the link to the encrypted version of the signed EMR data to a blockchain. Similarly, the encryption may have been performed using a key corresponding to the signing party to preserve confidentiality. In this manner, web-based EMR backup system 101 may facilitate the acknowledgement or signing of EMR data using a blockchain. In some embodiments, web-based EMR backup system 101 may store and/or manage modifications using database 103.

Similar to the acknowledgment or signing of EMR data, web-based EMR backup system 101 may manage EMR data editing and/or modification. For example, user devices 122, 124, and, 126 may participate in editing the EMR data. Web-based EMR backup system 101 may use a tokenization process to manage different versions of the EMR data corresponding to the different modifications.

Web-based EMR backup system 101 may manage this modification in a manner similar to generating EMR data so that the modified EMR data may be preserved using database 103 and/or a blockchain. The modified EMR data may be encrypted and stored as a modified version of the EMR data. Web-based EMR backup system 101 may generate a corresponding link to this encrypted version of the modified EMR data and/or generate a cryptographic hash of the modified EMR data. In some embodiments, web-based EMR backup system 101 may update an association corresponding to the EMR data link to access the modified EMR data. For example, a downstream user using the EMR data link may be directed to the modified version of the EMR data. The EMR data flow data structure may also be updated to track the modification. The EMR data owner may view this modification and/or accept or reject the modification. In some embodiments, downstream users may also be able to view the EMR data flow data structure to track the changes. In some embodiments, web-based EMR backup system 101 may create a separate EMR data token and/or EMR data link corresponding to the modified EMR data. Web-based EMR backup system 101 may publish the hash and/or the link to the encrypted version of the modified EMR data to a blockchain.

In embodiments of the invention, the web-based EMR backup system 101 (Spare Tire) includes a dashboard which is the main interaction point for authorized users. Various representations of the dashboard are illustrated in FIGS. 2-11 and described in detail below. In embodiments of the inventions, a Sign-In link is presented on the dashboard 200 of the web-based EMR backup system 101, and other pages. A Sign-Up link may also be shown. An affiliate or authorized person my sign in, with various means, such as, employee login credentials, mobile phone number and verification code, etc. A new person, or as an enterprise desiring to affiliate, may do so through the Sign-Up link. The detailed procedures are rather well-known for such registration and are not shown here. Once registered and logged in, the user's account information can be accessed from the graphical user interface ("GUI") button 202. The user accounts page, not shown here, displays various information, related to the user's use of the web-based EMR backup system 101.

Figure 2:
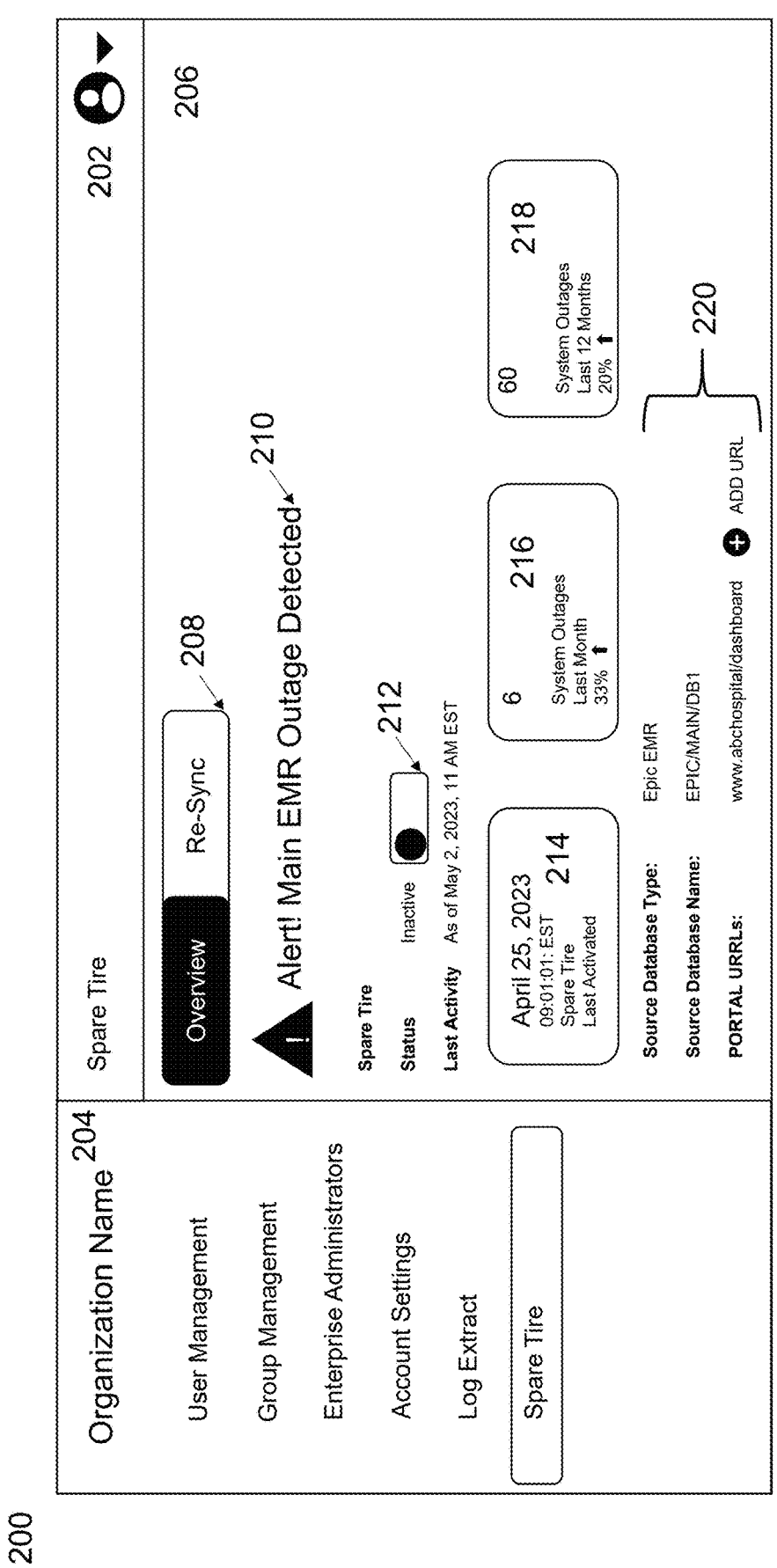
FIG. 2 illustrates a display for a web-based EMR backup system in an embodiment of the invention.

In embodiments of the invention the dashboard 200, as shown in FIG. 2, is utilized to display information pertinent to a user (medical professional or staff). As shown in FIG. 2, the dashboard includes an Organization tab 204 that allows a user to interact with the web-based EMR backup system 101 in a variety of ways, including, selecting the organization, managing the users or medical groups that access the web-based EMR backup system 101, managing the administrators that have access to the web-based EMR backup system 101, manage the settings of the web-based EMR backup system 101, extract event logs, and interact with the web-based EMR system 101's spare tire functionality.

When a user selects the Spare Tire icon within the Organization tab 204, the user is presented with various notifications, information, and settings related to the status of the web-based EMR backup system 101 in panel 206. The Spare Tire is the web-based EMR backup system 101 discussed throughout. The web-based EMR backup system 101 system monitors and replicates the EMR data contained within the database 107 of the Healthcare facilities' main EMR system 105 continuously and generates the information shown in panel 206.

GUI button 208 allows a user to switch between an overview panel 206 and a Re-Sync panel not shown. The overview panel displays notifications 210 related to the status of the web-based EMR backup system 101 as well as the main EMR system 105. Also displayed on the overview panel 206 is GUI button 212, which allows a user to activate and deactivate the web-based EMR backup system 101. GUI icons 214, 216, and 218 display various information and statistics related to the web-based EMR backup system 101 and the Main EMR system 105. For example, the GUI icon 214 may display the date and time of the last activation of the web-based EMR backup system 101. While GUI icons 216 and 218 display statistics and statistical trends such as, the total number of system outages that occurred during a timeframe and the percent increase from the previous timeframe referenced. For example, GUI icon 216 shows that the main EMR system 105 experienced an outage 6 times within the last month and is a 33% increase in month-to-month outages.

The overview panel 206 also displays various information 220 related to the main EMR system 105, such as the database type, name, and locator identifier, which allows access to the web-based EMR backup system 101.

Figure 4:
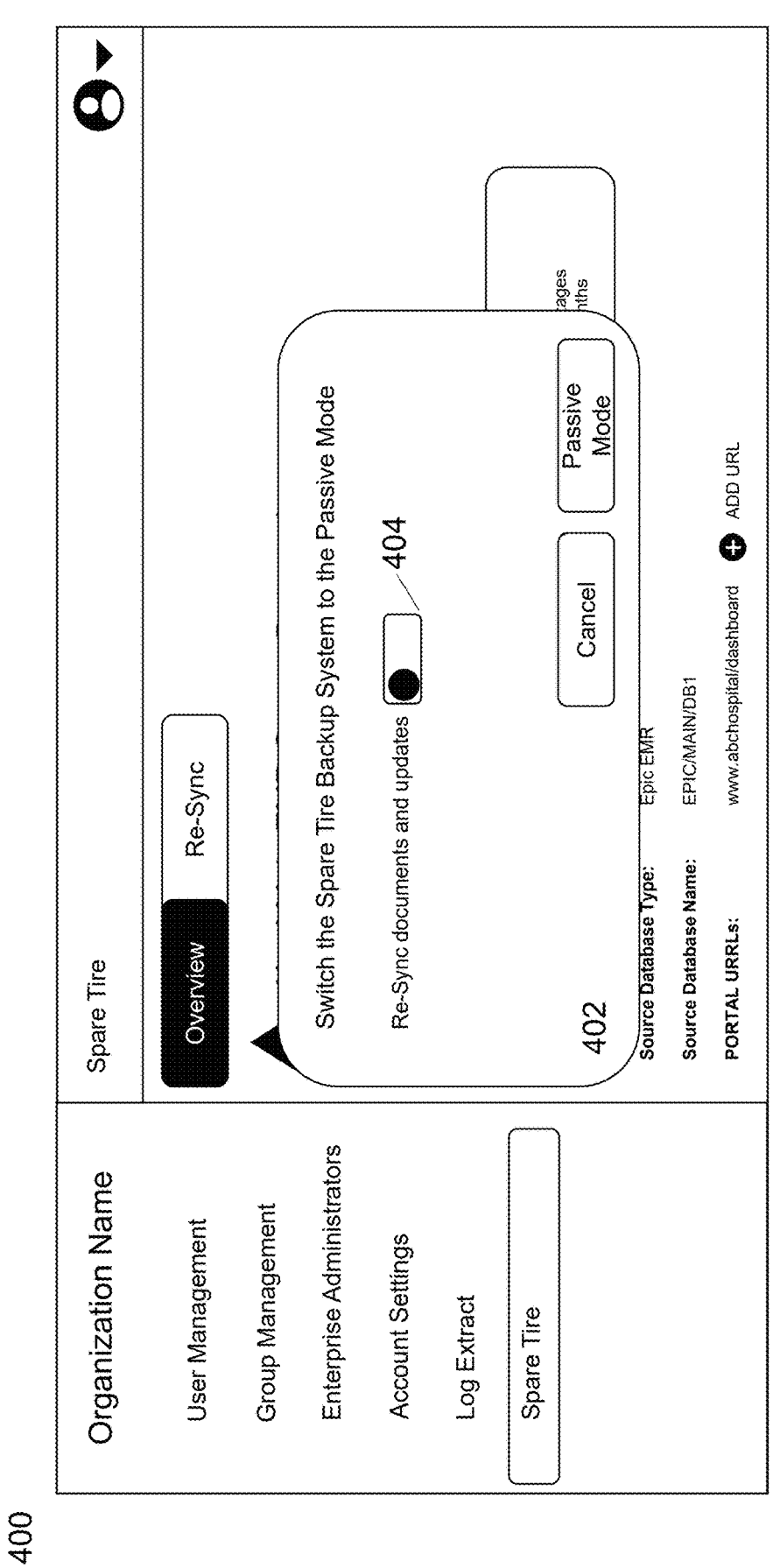
FIG. 4 illustrates a selectable reintegration process in an embodiment of the invention.

As stated above, GUI button 212 allows a user to activate and deactivate the web-based EMR backup system 101. The activated state is illustrated in FIG. 3. Once a user interacts with GUI button 212, a new window 402, as shown in FIG. 4, is displayed that asks the user to verify their intent to switch between the active and passive modes of the web-based EMR backup system 101. The window 402 also contains GUI button 404, which acts the user to determine if they want to reintegrate the EMR data that was changed or added while the main EMR system 105 was down using the Re-Sync process.

As stated above, the web-based EMR backup system 101 is continuously monitoring and replicating the EMR data in the main EMR database 105. The web-based EMR backup system 101 is also continuously monitoring and replicating the EMR data contained within the databases of enterprises 3-n. This allows the web-based EMR backup system 101 to build an accurate and up-to-date backup EMR database 103. Once an outage in the main EMR system 105 is detected, and the web-based EMR backup system 101 is activated using GUI button 212, the web-based EMR backup system 101 operates in the place of the main EMR system 105. That is, it allows medical professionals and staff to update and add EMR data using the web-based portal illustrated in FIGS. 2-11 as a part of their normal workflow. During their normal workflow, medical professionals and staff are required to update and add new EMR data pertaining to hospital administrative tasks, medical treatments, patient intake, patient charting, etc. This new EMR data is captured by the web-based portal illustrated in FIGS. 2-11 and processed by server 102 and stored in database 103. Once the main EMR system 105 is restored, the new EMR data that was created or updated during the outage needs to be reintegrated into the main EMR systems 105's databases 107. Reintegration is performed using the Re-Sync process of web-based EMR backup system 101. Once activated, the Re-sync process initiates API calls to main EMR system 105 to reintegrate all of the new and updated EMR data.

In embodiments of the invention, the web-based EMR backup system 101's ReSync process merges the new EMR data contained in database 103 with the old EMR data contained within the main EMR system 105's database 107. During the merging step, the web-based EMR backup system 101 determines specific EMR data that should be retained from the old EMR database 107 and specific EMR data that should be carried over from the new EMR data contained within the web-based EMR backup system 101's database 103. In some instances, the new EMR data stored in the database 103 will wholly substitute the EMR data within database 107. While in other instances, only a portion of the EMR data stored in database 103 will be carried over to database 107.

In embodiments of the invention, the Re-Sync process can be performed automatically, or without user action.

In embodiments of the invention, the Re-Sync process may be able to detect and reconcile errors arising from the reintegration process. During the Re-Sync process, there may be errors arising from the reconciliation of the EMR data within databases 103 and 107. These errors may arise due to changes within the new EMR data contained within database 103. For example, a data entry that was originally located within database 107 may have been entirely overwritten, edited, deleted, reformatted, etc and stored within database 103 during the main EMR system 105's network outage. Because the EMR data is no longer identical, an error may be displayed during reintegration. The web-based EMR backup system 101's Re-Sync process identifies these instances and sends a notification to the user that can be reviewed on the Re-Sync panel, not shown. Upon the selection of the notification, a user can review and resubmit the corrected EMR data to database 107.

In embodiments of the invention, the Re-Sync process automatically reviews and resubmits the corrected EMR data to database 107.

In embodiments of the invention, the Re-Sync process utilizes machine learning to automatically review and submit the corrected EMR data to database 107.

In embodiments of the invention, the web-based EMR backup system 101 may be configured to use a camera connected to user device 122, 124, or 126 to scan QR codes, barcodes, medication labels, etc. in order to quickly navigate the web-based EMR backup system 101's dashboard or generate/modify EMR data based on information obtained from the scanned QR code, barcode, or label. Some modern EMR systems allow medical personnel to scan medications, QR codes/barcodes on patient's wristbands, QR codes/barcodes on medications, QR codes/barcodes on medical equipment. For example, when a nurse enters a patient's hospital room, the nurse scans the QR code/barcode on the patient's wristband. In response, the web-based EMR backup system 101 will analyze the image and determine the patient's medical record number from the image. The web-based EMR backup system 101 will then open the detailed patient portal on the user device 122, 124, or 126. If a medication is scanned using a user device 122, 124, or 126, the web-based EMR backup system 101 will similarly analyze the image and determine the type of medication that was scanned. If a patient is scan before a medication, or the detailed patient port is open in the web-based EMR backup system 101's dashboard, the web-based EMR backup system will generate a medication administration record ("MAR") window based on an analysis of the EMR data in the patient's file and the medication scanned. This MAR window identifies the proper dosage of the medication scanned and will also verify that the medication is approved for the selected patient. Approval is determined based on an analysis of the EMR data that look at the patient's allergies, listed medications, doctor's orders, etc.

If a piece of medical equipment is scanned, the web-based EMR backup system 101 may generate instructions for proper usage, calibration, etc. The web-based EMR backup system 101 may also prompt the user to connect the user device 122, 124, or 126 to the piece of medical equipment using a wired or wireless communication connection. Once connected, the web-based EMR backup system 101 may be able to control, calibrate, or read information provided by the medical equipment. The medical equipment can be a bedside patient monitor capable of monitoring a patient's SpO2 sats, heart rate, respirations, etc. The medical equipment may also be an IV Fluid dispenser configured to dispense intravenous medications and fluids. The medical equipment may also be a type of medical imaging device, such as, x-ray, MRI, CT, bed status sensor, etc. The web-based EMR backup system 101 may pull data from these various medical devices and use the data collected to update the EMR data contained with database 103. For example, the web-based EMR backup system 101 obtain a patient's live vital signs using a beside monitor and use the live data collected to update the EMR data contained within the database 103. This allows medical personnel the ability to maintain efficiency and optimal workflows in the event of a planned downtime or cyber attack. As stated above, the web-based EMR backup system 101 may also be configured to control the medical devices. The web-based EMR backup system 101 may allow medical personnel to change the dosage of an intravenous medication or fluid using the web-based EMR backup system 101's dashboard. After a modification is made, the web-based EMR backup system 101 logs the modifications to the EMR data and stores the updates in database 103.

In embodiments of the invention, the web-based EMR backup system 101's web portal includes a dashboard designed for medical personnel and staff. Representations of this dashboard are illustrated in FIGS. 5-11. The web-based EMR backup system 101 generates of the panels illustrated in FIGS. 5-11 using the EMR data contained in database 103. The medical personnel and staff dashboard 500 provides medical personnel and staff with the resources and information needed to provide effective and efficient care of patients. GUI tab 502 includes GUI buttons (Home Page, Patients, Help & Support, etc.) that allow medical personnel and staff to navigate various areas of the web-based EMR backup system 101. For example, if "Home Page" is selected, a new page is displayed, not shown, that summarizes all of the information pertinent to the employee currently signed in, such as, personalized patient lists, new orders/active orders, medications due, treatment schedules, text chat, work calendar, notifications, continuing education tab, and alerts, etc. If "Help & Support" is selected, a new page is displayed, not shown, that contains information such as, troubleshooting tips, support text chat, IT text chat, help documents, contact information, etc.

Figure 6:
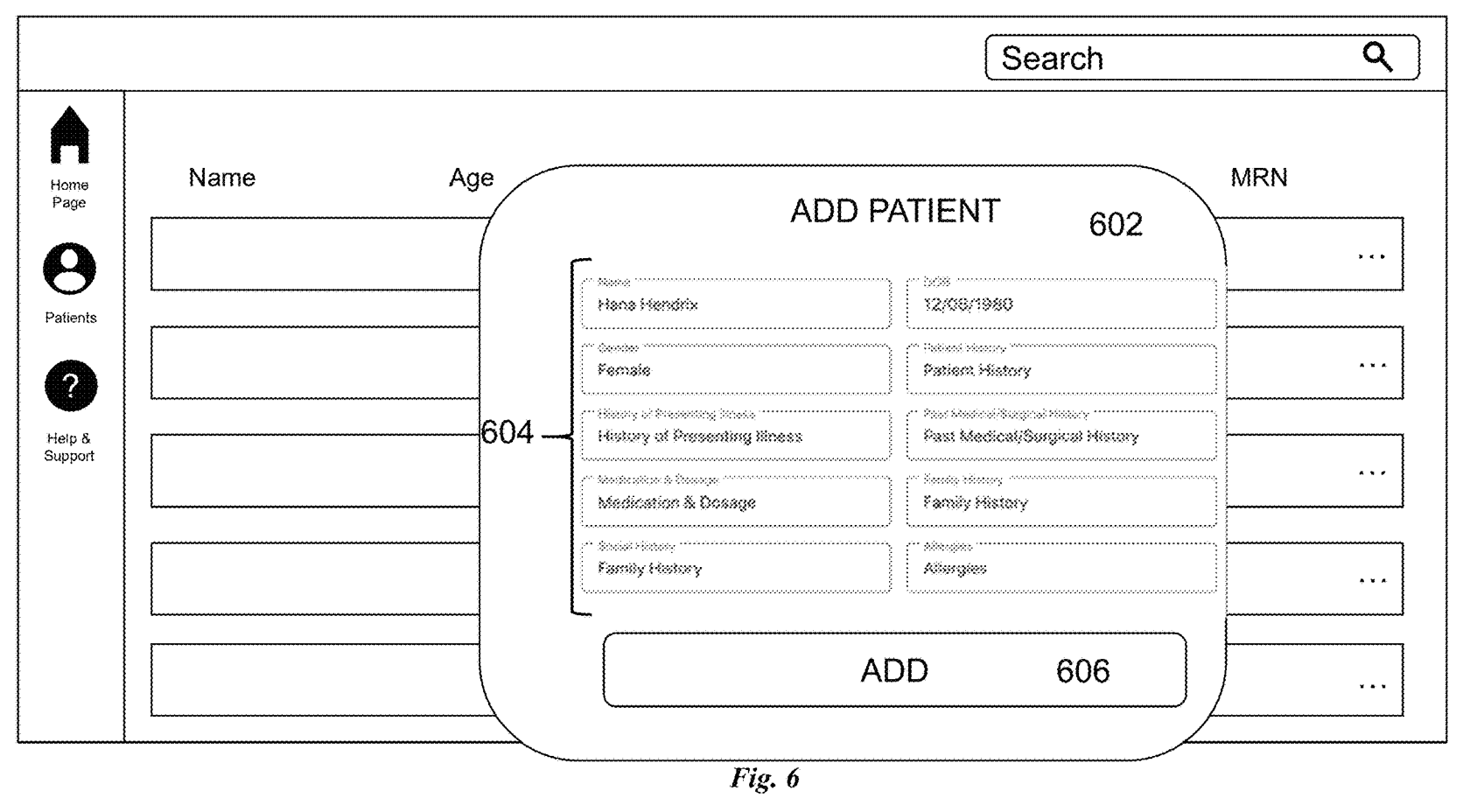

In embodiments of the invention, when a user selects the "Patient" icon, panel 506 is displayed. Panel 506 displays a list of all patients within the main EMR system 105's database 107. Each patient entries 508A-508E contain a summary of the patient's EMR data. For example, patient entries 508A-508E includes the patients name, age, sex, date of birth, medical record number ("MRN"), etc. Patient entries 508A-508D can be search for using search bar 504. A medical employee can also add new patients using GUI button 510. Upon the selection of GUI button 510, a new graphical element 602, shown in FIG. 6, is displayed that contains various electronic data entry fields 604. The electronic data entry fields prompt a medical employee to enter in patient EMR data such as, name, date of birth, gender, patient history, history or presenting illness, past medical/surgical history, medication and dosage, family history, social history, allergies, etc. Once the electronic data entry files 604 and filed out, the medical employee can submit the new patient form using GUI button 606.

Figure 7:
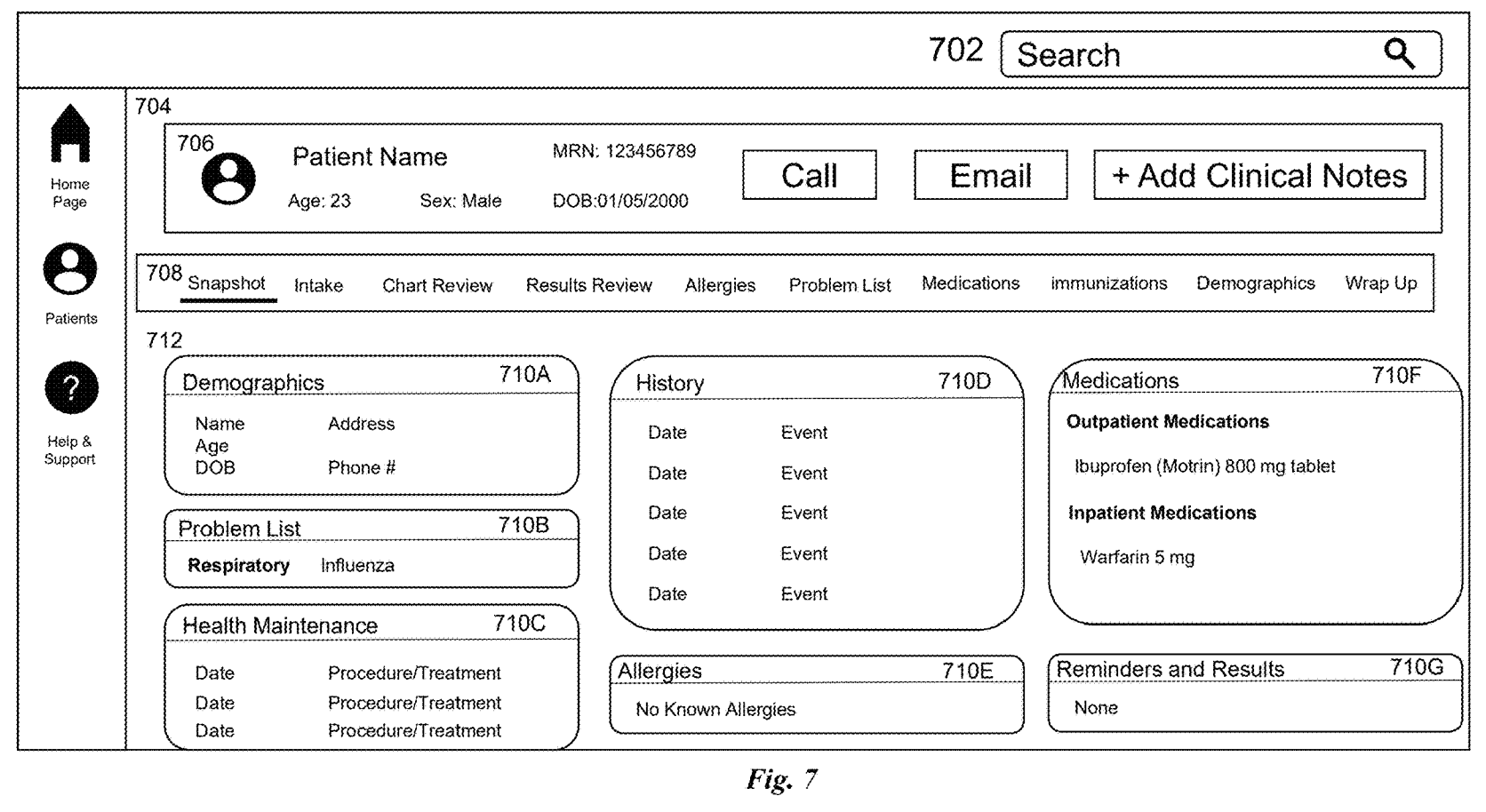

In embodiments of the invention, the web-based EMR backup system 101's patient entries 508A-508E can be selected, which causes a detailed patient portal to be displayed as illustrated in FIG. 7. The detailed patient portal 700 includes a search bar 702 that allows a medical employee to search for EMR data contained within the currently selected patient's EMR data file. The detailed patient portal 700 also includes a panel 704 that contains detailed patient EMR data corresponding to the patient selected from the patient entries 508A-508E. Panel 704 contains a summary panel 706, navigation panel 708, and EMR Data Panels 710A-710G. Summary panel 706 contains a small glimpse of the EMR data for the selected patient including, but not limited to, patient name, age, sex, MRN, date of birth, phone number, email address etc. The summary panel 706 also may include GUI buttons that enable the medical employee to initiate a call to the selected patient, email the selected patient, or add clinical notes to the selected patients EMR data file.

Navigation Panel 708 includes various links to web pages generated using the EMR data that contain information pertinent to medical employees such as, snapshots of the patient's entire EMR data file, electronic intake forms, chart review (patient's chart), results review (test results), allergies, problem list, medications, immunizations, demographics, Medication Administration Records ("MAR"), new/active orders, etc. When a user selects on of the icons listed in the navigation panel 708, the information presented in panel 712 is generated using the EMR data stored within database 103. The information presented in panel 712 changes depending on the icon selected in the navigation panel 708. For example, when the "Snapshot" icon is selected, panel 712 generates a snapshot of the selected patient's entire EMR file using subpanels 710A-710G as shown in FIG. 7. Subpanels 710A-710G provides the medical employee with organized information related to the selected patient. For example, subpanel 710D is titled "History" and includes the date and medical event that occurred on each data, while subpanel 710C includes the date and the procedure or treatment administered on each date.

Figure 8:
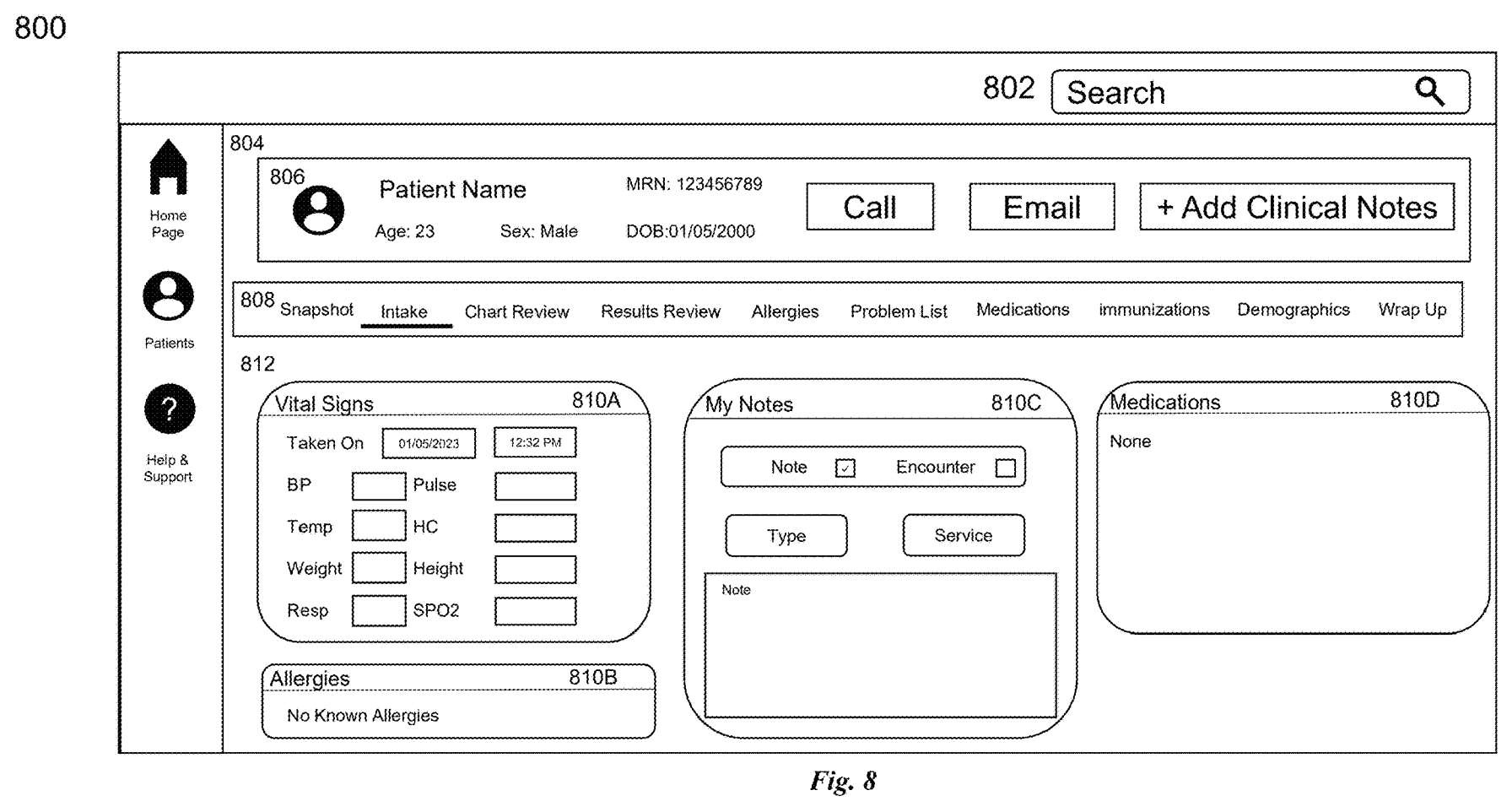

Selecting the "Intake" icon on the navigation panel 708 causes panel 712 to generate an electronic form for the selected patient as shown in FIG. 8. Intake panel 812 displays various subpanels 810A-810D, which allow a medical employee to input EMR data pertaining to the selected patient. For example, subpanel 810A allows the medical employee to enter the patient's vital signs, while simultaneously attaching a date and time to the modification. Similarly, subpanel 810C allows a medical employee to draft a clinical note that will be added to the patient's EMR data file.

Figure 9:
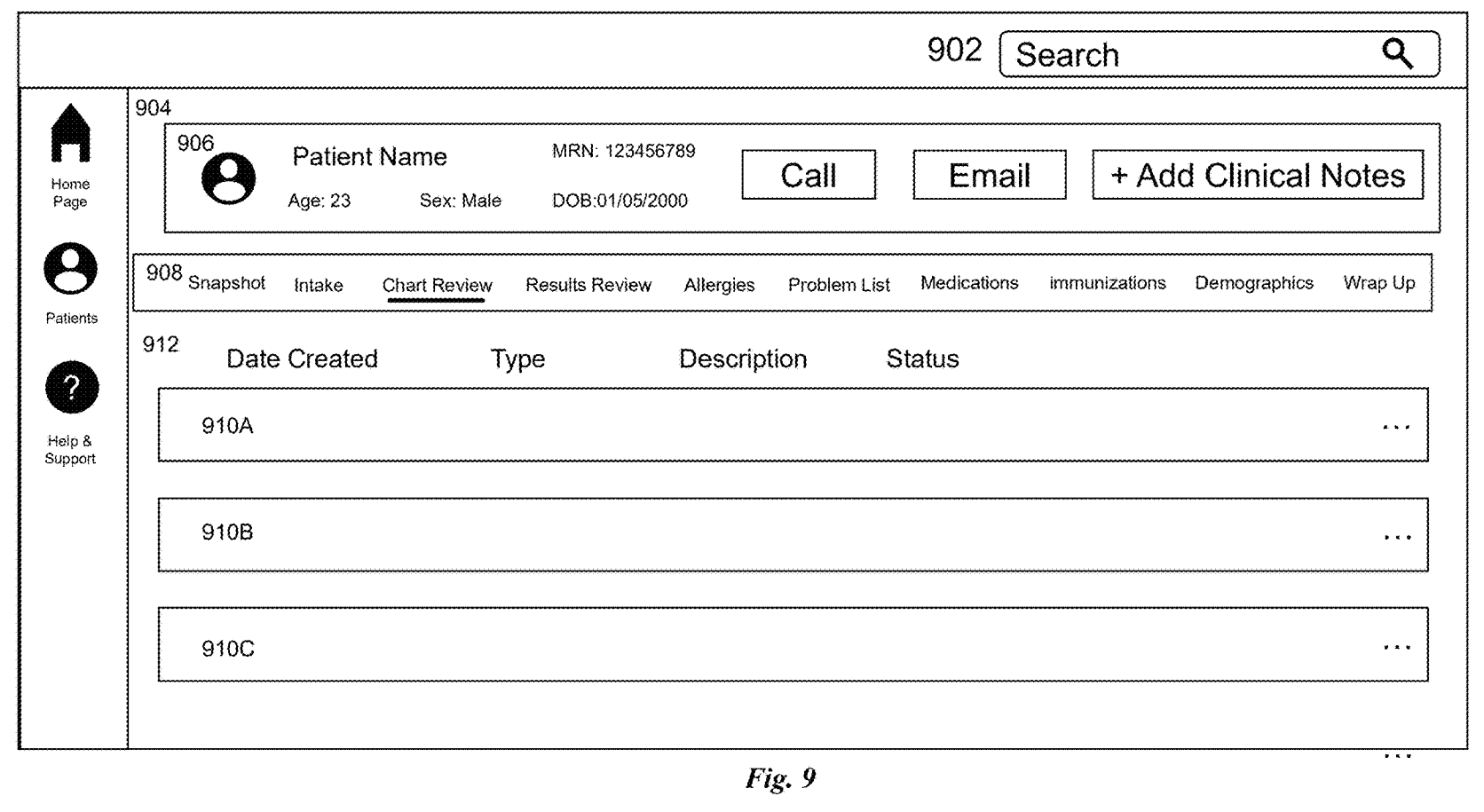

Selecting the "Chart Review" icon on the navigation panel 708 causes panel 712 to generate a patient chart display illustrated in FIG. 9. As shown in FIG. 9, the chart review panel 912 contains patient chart entries 910A-910C. These chart entries may include information such as, the date the entry was created, the type of entry, a description of the entry, a status of the entry, etc. Furthermore, patient chart entries 910A-910C can be selected by the medical employee, which generates a detailed view of each patient chart entries 910A-910C, not shown. Patient chart entries 910A-910C can also be added and modified by medical employees.

Figure 11:
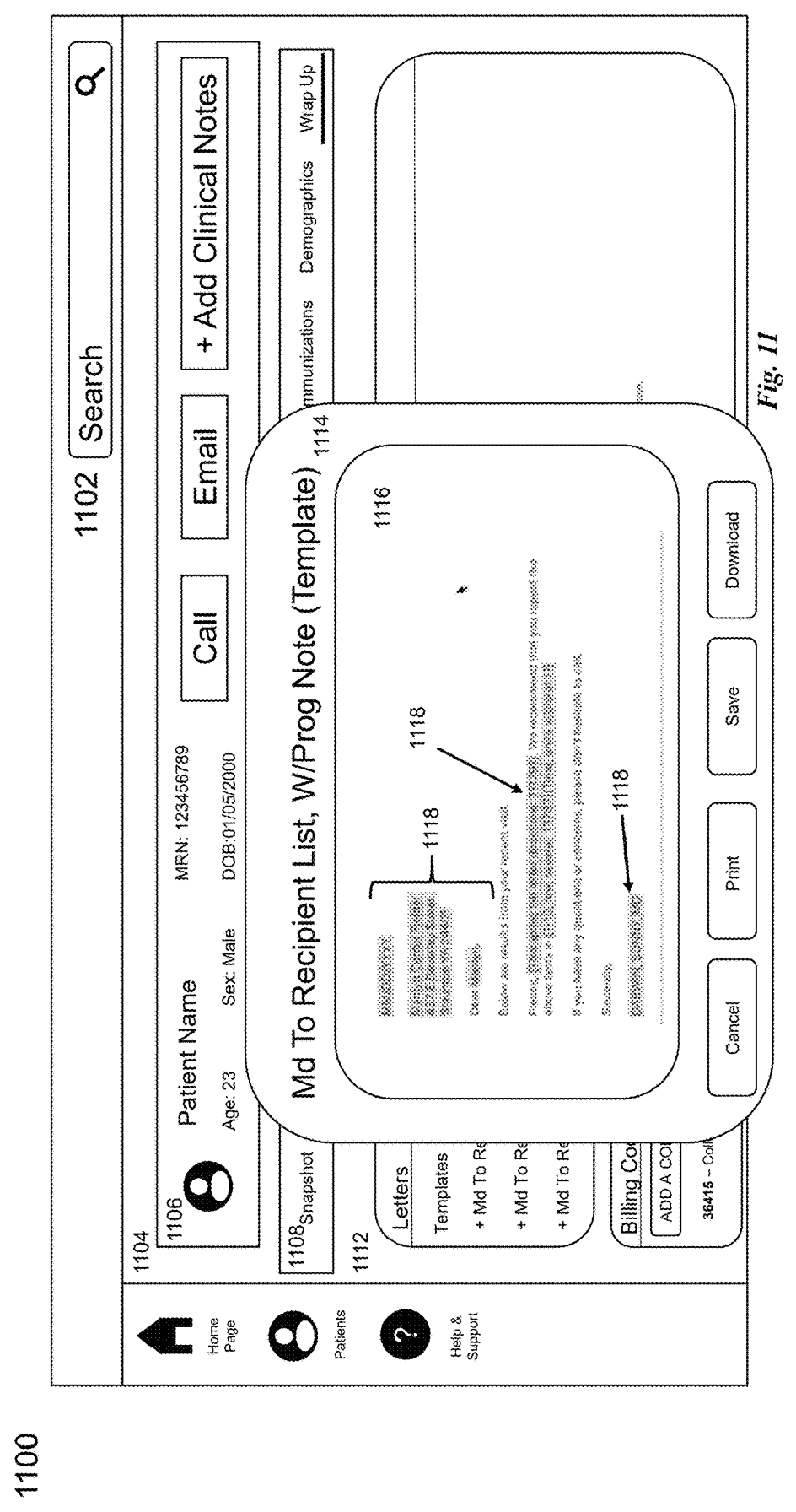

Selecting the "Wrap Up" icon on the navigation panel 708 causes panel 712 to generate a discharge panel 1012 as shown in FIG. 10. The discharge panel 1012 includes subpanels 1010A-1010C, which corresponding to EMR data related to the discharging of a patients, such as, letters, billing codes, patient instructions, etc. Subpanel 1010A generates list of electronic templates that can be modified, saved, and sent, to patients, insurance companies, other medical employees, other enterprises 2-n, etc. An example of one possible electronic template is illustrated in FIG. 11 and described below. Subpanel 1010B generates a list of billing code associated with the patient's most recent visit. A medical employee can add, review, edit, and remove billing codes using subpanel 1010B. Patient medical bills can also be generated, either manually or automatically, using the discharge panel 1012. Subpanel 1010C is generated using the EMR data and includes electronic patient instructions. The patient instructions can be manually generated by a medical employee by selecting the desired documents or automatically generated by analyzing the patient's EMR data. Furthermore, the letters, bills, and patient instructions can be manually or automatically shared with the patient, other medical employee, other enterprise 2-n, etc.

FIG. 11 shows an exemplar of the electronic templates from subpanel 1010A. When a medical employee selects one of the electronic templates from subpanel 1010A, window 1114 is generated. Window 1114 allows a user to edit, print, save, or download the electronic template. Furthermore, the electronic templates may include portions that are auto-generated using the EMR data stored in database 103. For example, electronic template 1116, includes data fields 1118 which include information such as, date, time, address, patient's name, doctor's name, summary of treatment, summary of patient instructions, summary of medications and dosages, etc. A medical employee may also manually input the information into data fields 1118.

Figure 12:
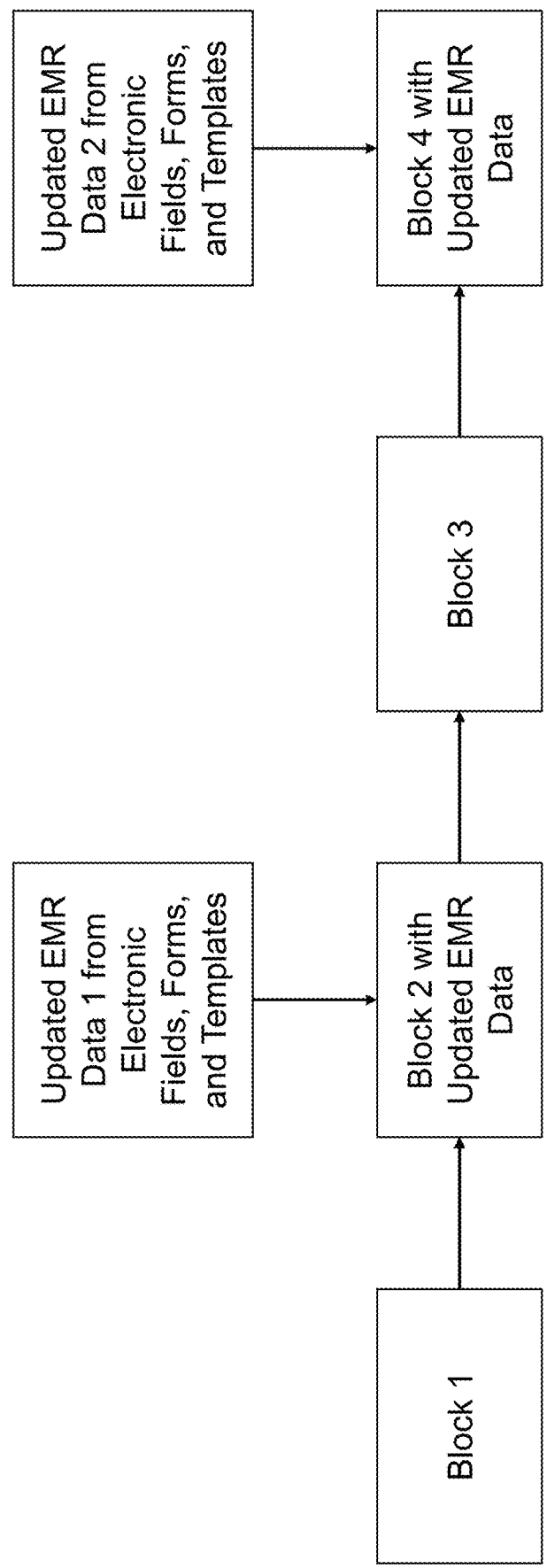
FIG. 12 illustrates Blockchain interaction in an embodiment of the invention.

FIG. 12 is a simplified block diagram illustrating creation and revision of EMR data, electronic data fields, electronic forms, and electronic templates, using API calls. Once the API call is initiated due to a modification/creation, it is assigned with a Blockchain wallet and submitted to the Blockchain. If the EMR data is a letter, template, or form, a smart form is created for it and invitations are sent to the desired recipients. All users and enterprises are assigned Blockchain wallets (i.e. Private Keys) and all their interactions regarding EMR data is stored, verified, and included in the block.

Various embodiments throughout have been described using a blockchain and blockchain elements. In an embodiment, the web-based EMR backup system 101 is implemented without the use of a blockchain and without submitted EMR data changes to the blockchain. To ensure network and data security, traditional methods of securing a data network may be used, such as, encryption.

Figure 13:
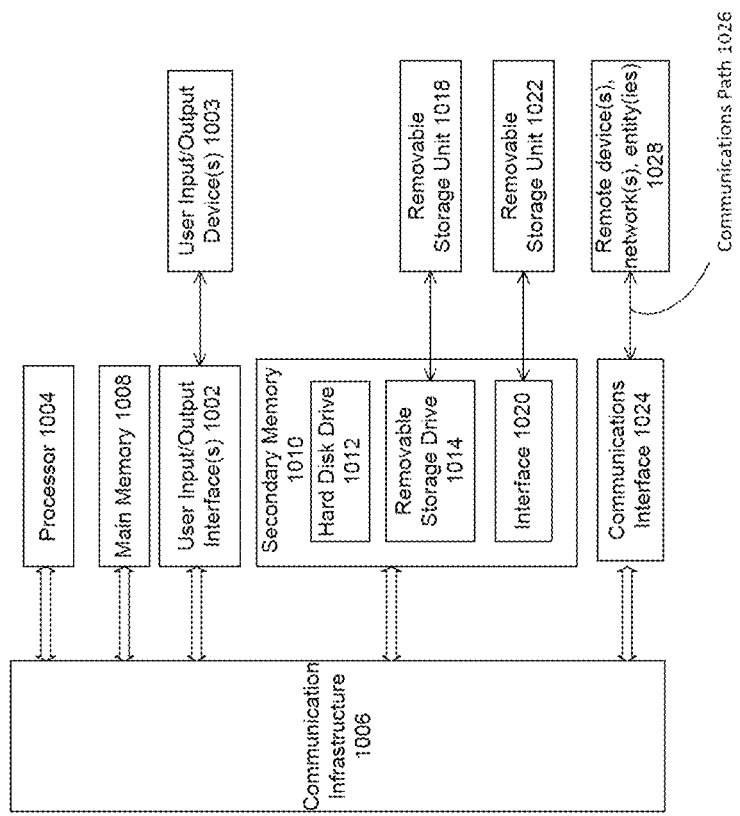
FIG. 13 depicts an example computer system useful for implementing various embodiments.

Various embodiments may be implemented, for example, using one or more well-known computer systems, such as computer system 1300 shown in FIG. 13. One or more computer systems 1300 may be used, for example, to implement any of the embodiments discussed herein, as well as combinations and sub-combinations thereof.

Computer system 1300 may include one or more processors (also called central processing units, or CPUs), such as a processor 1304. Processor 1304 may be connected to a communication infrastructure or bus 1306.

Computer system 1300 may also include user input/output device(s) 1303, such as monitors, keyboards, pointing devices, etc., which may communicate with communication infrastructure 1306 through user input/output interface(s) 1302.

One or more of processors 1304 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 1300 may also include a main or primary memory 1308, such as random access memory (RAM). Main memory 1308 may include one or more levels of cache. Main memory 13008 may have stored therein control logic (i.e., computer software) and/or data.

Computer system 1300 may also include one or more secondary storage devices or memory 1310. Secondary memory 1310 may include, for example, a hard disk drive 1312 and/or a removable storage device or drive 1314. Removable storage drive 1314 may be a floppy disk drive, a magnetic tape drive, a compact disk drive, an optical storage device, tape backup device, and/or any other storage device/drive.

Removable storage drive 1314 may interact with a removable storage unit 1318. Removable storage unit 1318 may include a computer usable or readable storage device having stored thereon computer software (control logic) and/or data. Removable storage unit 1318 may be a floppy disk, magnetic tape, compact disk, DVD, optical storage disk, and/any other computer data storage device. Removable storage drive 1314 may read from and/or write to removable storage unit 1318.

Secondary memory 1310 may include other means, devices, components, instrumentalities or other approaches for allowing computer programs and/or other instructions and/or data to be accessed by computer system 1300. Such means, devices, components, instrumentalities or other approaches may include, for example, a removable storage unit 1322 and an interface 1320. Examples of the removable storage unit 1322 and the interface 1320 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 1300 may further include a communication or network interface 1324. Communication interface 1324 may enable computer system 1300 to communicate and interact with any combination of external devices, external networks, external entities, etc. (individually and collectively referenced by reference number 1328). For example, communication interface 1324 may allow computer system 1300 to communicate with external or remote devices 1328 over communications path 1326, which may be wired and/or wireless (or a combination thereof), and which may include any combination of LANs, WANs, the Internet, etc. Control logic and/or data may be transmitted to and from computer system 1300 via communication path 1326.

Computer system 1300 may also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computer system 1300 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 1000 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards. For example, an industry standard format such as Fast Healthcare Interoperability Resource (FHIR) created by the Health Level Seven (HL7) International standards organization may be used.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 1300, main memory 1308, secondary memory 1310, and removable storage units 1318 and 1322, as well as tangible articles of manufacture embodying any combination of the foregoing. Such control logic, when executed by one or more data processing devices (such as computer system 1300), may cause such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 13. In particular, embodiments can operate with software, hardware, and/or operating system implementations other than those described herein.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc. using orderings different than those described herein.

References herein to "one embodiment," "an embodiment," "an example embodiment," or similar phrases, indicate that the embodiment described can include a particular feature, structure, or characteristic, but every embodiment can not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents.

What is claimed is:

1. A computer implemented method, comprising:
receiving, by one or more of a plurality of internet-connected servers and an EMR backup server, EMR data;
storing, by one or more of the plurality of internet-connected servers and the EMR backup server, the EMR data;
providing, by the EMR backup server, a web portal;
connecting a user device to the EMR backup server;
receiving, via the user device, a user selection of an activation button;
in response to receiving the user selection of the activation button, transmitting, from the EMR backup server, a location identifier corresponding to the web portal to the user device;
displaying, by the EMR backup server, the web portal, wherein the web portal includes a dashboard, wherein the dashboard is generated by the EMR data and includes one or more input fields for a user to submit additional EMR data;
receiving, via the user device, additional EMR data, wherein the additional EMR data is provided by a user input in the one or more input fields;
generating, by the EMR backup server, a reintegration flag;
updating, by the EMR backup server, the EMR data based on the additional EMR data; and
storing, by the EMR backup server, the updated EMR data.

2. The computer implemented method of claim 1, further comprising:
receiving, via the user device, a user selection of a deactivation button;
in response to receiving the user selection of the deactivation button, transmitting, from the EMR backup server to the one or more of the plurality of internet-connected servers, a request to reintegrate the EMR data stored on the EMR backup server with the EMR data stored on the one or more of the plurality of internet-connected servers.

3. The computer implemented method of claim 2, further comprising:
receiving, by the one or more of the plurality of internet-connected servers, the request to reintegrate the EMR data;
in response to receiving the request to reintegrate the EMR data, requesting, from the EMR backup server, the reintegration flag, wherein the reintegration flag identifies EMR data that has been added or updated during a network outage;
generating, by the one or more of the plurality of internet-connected servers, an updated EMR database based on the reintegration flag;
storing, by the one or more of the plurality of internet-connected servers, the updated EMR database.

4. The computer implemented method of claim 1, where in the dashboard includes a clinical notes data field that is electronically signed using a hash of a user's profile and the EMR data.

5. The computer implemented method of claim 1, wherein the dashboard includes one or more electronic forms.

6. The computer implemented method of claim 5, wherein the electronic forms includes templates for patient letters and instructions that are automatically generated using the EMR data.

7. The computer implemented method of claim 1, wherein the method further comprises,
generating, by the EMR backup server, a hash of the EMR data;
storing, by the EMR backup server, the hash on a blockchain.

8. The computer implemented method of claim 1, wherein the method further comprises, wherein the dashboard includes data fields for patient admission and discharge, clinical notes, chart review, order transmittal, ambulatory workflow, patient transfer, and bed status.

9. An internet based web-based EMR backup system, comprising:
an EMR backup server registering one or more of a plurality of Internet-connected servers,
the one or more of the plurality of Internet-connected servers hosting respective websites,
the EMR backup server providing configurable coded instructions to the one or more of the plurality of Internet-connected servers for displaying an activation button on the respective websites; and a user device connected to the one or more of the plurality of Internet-connected servers,
wherein each of the one or more of the plurality of Internet-connected servers are configured to:
display the activation button on a respective website of the Internet-connected server's using the configurable coded instructions received from the EMR backup server;
receive, via the user device, a user selection of the activation button via the respective website of Internet-connected server's;
in response to receiving the user selection of the activation button, transmit a web portal to the user device, wherein the web portal includes a dashboard that is generated by EMR data and includes one or more input fields for a user to submit additional EMR data;
receive, via the user device, additional EMR data, wherein the additional EMR data is provided by a user input in the one or more input fields;
generate a reintegration flag;
update the EMR data based on the additional EMR data;
generate a hash of the updated EMR data; and
store the updated EMR data.

10. The internet based web-based EMR backup system of claim 9, wherein the one or more of the plurality of Internet-connected servers are further configured to:
receive, via the user device, a user selection of a deactivation button;
in response to receiving the user selection of the deactivation button, transmit a request to reintegrate the EMR data stored on the EMR backup server with the EMR data stored on the one or more of the plurality of internet-connected servers.

11. The internet based web-based EMR backup system of claim 10, wherein the one or more of the plurality of Internet-connected servers are further configured to:
receive the request to reintegrate the EMR data;
in response to receiving the request to reintegrate the EMR data, requesting, from the EMR backup server, the reintegration flag, wherein the reintegration flag identifies EMR data that has been added or updated during a network outage;
generate an updated EMR database based on the reintegration flag;
store the updated EMR database.

12. The internet based web-based EMR backup system of claim 9, where in the dashboard includes a clinical notes data field that is electronically signed using a hash of a user's profile and the EMR data.

13. The internet based web-based EMR backup system of claim 9, wherein the dashboard includes one or more electronic forms.

14. The internet based web-based EMR backup system of claim 13, wherein the electronic forms includes templates for patient letters and instructions that are automatically generated using the EMR data.

15. The internet based web-based EMR backup system of claim 9, further comprising,
generating, by the EMR backup server, the hash of the EMR data;
storing, by the EMR backup server, the hash on a blockchain.

16. The internet based web-based EMR backup system of claim 9, further comprising, wherein the dashboard includes data fields for patient admission and discharge, clinical notes, chart review, order transmittal, ambulatory workflow, patient transfer, and bed status.

17. A non-transitory computer-readable device having instructions stored thereon that, when executed by at least one computing device, cause the at least one computing device to perform operations comprising:
receiving, by one or more of a plurality of internet-connected servers and an EMR backup server, EMR data;
storing, by one or more of the plurality of internet-connected servers and the EMR backup server, the EMR data;
providing, by the EMR backup server, a web portal;
connecting a user device to the EMR backup server;
receiving, via the user device, a user selection of an activation button;
in response to receiving the user selection of the activation button, transmitting, from the EMR backup server, a location identifier corresponding to the web portal to the user device;
displaying, by the EMR backup server, the web portal, wherein the web portal includes a dashboard, wherein the dashboard is generated by the EMR data and includes one or more input fields for a user to submit additional EMR data;
receiving, via the user device, additional EMR data, wherein the additional EMR data is provided by a user input in the one or more input fields;
generating, by the EMR backup server, a reintegration flag;
updating, by the EMR backup server, the EMR data based on the additional EMR data; and
storing, by the EMR backup server, the updated EMR data.

18. The non-transitory computer-readable device of claim 17, further comprising:
receiving, via the user device, a user selection of a deactivation button;
in response to receiving the user selection of the deactivation button, transmitting, from the EMR backup server to the one or more of the plurality of internet-connected servers, a request to reintegrate the EMR data stored on the EMR backup server with the EMR data stored on the one or more of the plurality of internet-connected servers.

19. The non-transitory computer-readable device of claim 18, further comprising:
receiving, by the one or more of the plurality of internet-connected servers, the request to reintegrate the EMR data;
in response to receiving the request to reintegrate the EMR data, requesting, from the EMR backup server, the reintegration flag, wherein the reintegration flag identifies EMR data that has been added or updated during a network outage;
generating, by the one or more of the plurality of internet-connected servers, an updated EMR database based on the reintegration flag;
storing, by the one or more of the plurality of internet-connected servers, the updated EMR database.

20. The non-transitory computer-readable device of claim 17, wherein the dashboard includes a clinical notes data field that is electronically signed using a hash of a user's profile and the EMR data.

21. The non-transitory computer-readable device of claim 17, wherein the dashboard includes one or more electronic forms.

22. The non-transitory computer-readable device of claim 21, wherein the electronic forms includes templates for patient letters and instructions that are automatically generated using the EMR data.

23. The non-transitory computer-readable device of claim 17, further comprising:
   generating by the EMR backup server, a hash of the EMR data;
   storing, by the EMR backup server, the hash on a blockchain.

24. The non-transitory computer-readable device of claim 17, further comprising, wherein the dashboard includes data fields for patient admission and discharge, clinical notes, chart review, order transmittal, ambulatory workflow, patient transfer, and bed status.

* * * * *